US00PP11816P2

(12) United States Plant Patent
Degenhardt

(10) Patent No.: US PP11,816 P2
(45) Date of Patent: Mar. 13, 2001

(54) AGASTACHE PLANT NAMED 'RED FORTUNE'

(75) Inventor: Dick Degenhardt, Boskoop (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/263,856

(22) Filed: Mar. 8, 1999

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Agastache plant named 'Red Fortune', characterized by its upright plant habit; dark green leaf color; purple red flower color; freely flowering with numerous flowers per spike; and resistance to pathogens common to *Agastache mexicana*.

2 Drawing Sheets

BACKROUND OF THE INVENTION

The present invention relates to a new and distinct cultivar of Agastache plant, botanically known as *Agastache mexicana*, and hereinafter referred to by the cultivar name 'Red Fortune'.

The new Agastache was discovered by the Inventor in Boskoop, The Netherlands, in 1996 in a seed bed of sown *Agastache mexicana* seed from various crosses of unnamed Agastache seedling selections. The new Agastache was selected as an individual seedling in the progeny of this crossing on the basis of its purple red flower color and large inflorescence size.

Compared to plants of the unnamed selections of *Agastache mexicana*, plants of the new Agastache are shorter, have a deeper purple red flower color, flower for a longer period of time and are more hardy.

Asexual propagation of the new cultivar by vegetative cuttings taken at Boskoop, The Netherlands, has shown that the unique features of this new Agastache are stable and reproduced true to type in successive generations.

SUMMARY OF THE INVENTION

Plants of the cultivar 'Red Fortune' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Red Fortune'. These characteristics in combination distinguish 'Red Fortune' as a new and distinct cultivar:

1. Upright plant habit.
2. Dark green leaf color.
3. Purple red flower color.
4. Freely flowering with numerous flowers per spike.
5. Resistant to pathogens common to *Agastache mexicana*.

BRIEF DESCRIPTION OF THE PHOTOGRAPHS

The accompanying colored photographs illustrate the overall appearance of the cultivar, showing the colors as true as it is reasonably possible to obtain in colored reproductions of this type.

The photograph on the first sheet comprises a top perspective view of a typical plant of the new Agastache in a container.

The photograph on the second sheet comprises a close-up view of typical leaves of the new Agastache. Flower and foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were one-year old plants grown under outdoor production conditions which closely approximate commercial production conditions during the spring and summer in Boskoop, The Netherlands.

Botanical classification: *Agastache mexicana* cultivar 'Red Fortune'.

Parentage:

*Female parent.*—Unnamed *Agastache mexicana* seedling selection.

*Male parent.*—Unnamed *Agastache mexicana* seedling selection.

Propagation:

*Type.*—By vegetative cuttings.

*Time to initiate and develop roots.*—About 14 days during the spring under outdoor production conditions, average temperature about 15° C.

*Rooting habit.*—Numerous and fine.

Plant description:

*Crop time.*—From cuttings, about four to five months are required to produce fully-grown flowering plants.

*Form.*—Upright, monopodial, perennial herb.

*Branching habit.*—Flowering stems arise from the roots; moderate branching from the stems, typically 6 to 8 lateral branches.

*Plant height.*—About 70 to 90 cm.

*Area of spread.*—About 40 to 50 cm.

*Vigor.*—Moderate to vigorous.

*Main stems.*—Diameter: About 4 mm. Internode length: About 6 to 12 cm. Cross section: Square.

Texture: Covered with very short grayish-brown hairs. Color: 138A.

*Foliage description.*—Arrangement: Single; opposite. Quantity per main stem: Typically about 16 to 20. Length: About 4 to 6.5 cm. Width: About 1.8 to 3.5 cm. Aspect: Mostly horizontal. Shape: Lanceolate to ovate. Apex: Acute. Base: Obtuse. Margin: Towards apex, entire; towards base, serrate. Texture: Lower surface, pubescent. Fragrance: Strong peppermint scent when rubbed. Color: Young and mature foliage, upper surface: 137A. Young and mature foliage, lower surface: 138B. Ventation, upper surface: 137A. Venation, lower surface: 148B. Petiole: Length: About 1.5 to 1.8 cm. Diameter: About 1.5 to 2 mm. Color: 148B.

Flower description:

*Flower type and habit.*—Numerous labiate single flowers arranged in verticillasters arranged in terminal spikes. Freely flowering with about 1,500 to 1,700 flowers and flower buds per plant.

*Natural flowering season.*—Continuously flowering typically during August through September in the Northern Hemisphere.

*Flower longevity.*—Flowers last about one week on the plant and more than one week as a cut flower.

*Fragrance.*—None detected.

*Flower buds* (*about one day before opening*).—Length: About 1.2 to 1.3 cm. Diameter: About 2 to 3 mm. Shape: Obovate. Rate of opening: About five weeks from visible bud to fully opened flower. Color: 63A.

*Flower size.*—Length: About 1.9 to 2.1 cm. Diameter: About 6 mm.

*Petals.*—Arrangement: Corolla two-lipped. Upper lip erect, two-lobed; lower lip, three-lobed. Shape: Oblanceolate. Apex: Acute to obtuse. Margin: Entire. Length: About 1.9 to 2.1 cm. Texture: Satiny; scabrous, very short hairs. Color: When opening and fully opened flower, upper surface: 64A to 67A; color fading to 64C with subsequent development. When opening and fully opened flower, lower surface: 63A.

*Sepals.*—Arrangement: Calyx tubular or campanulate, five-toothed, upper teeth longer than lower. Apex: Acuminate. Margin: Entire. Calyx length: About 9 to 11 mm. Calyx width: About 2 to 3 mm. Texture: Dull; scabrous, densely covered with very short hairs. Color, upper and lower surfaces: When opening, close to 138B; fully opened, 184A to 184B.

*Pedicels.*—Length: About 1 to 2 mm. Angle: About 40 to 50° C. to stem. Strength: Moderately strong. Color: 138B.

*Reproductive organs.*—Stamens: Stamen number: About four. Anther attachment: Dorsifixed. Anther size: About 0.7 to 1 mm. Anther color: Black. Pollen amount: Sparse. Pollen color: Creamy white. Pistils: Pistil number: One. Pistil length: About 1.9 to 2.1 cm. Stigma shape: Recurved, three-parted. Stigma color: 64A to 67A. Style length: About 1.7 to 1.9 cm. Style color: 64A to 67A, much paler at base. Ovary color: 144B.

*Seed.*—Length: About 1 mm. Diameter: About 1 mm.

Disease resistance: Under commercial conditions, plants of the new Agastache have exhibited good resistance to diseases common to Agastache.

It is claimed:

1. A new and distinct cultivar of Agastache plant named 'Red Fortune', as illustrated and described.

* * * * *

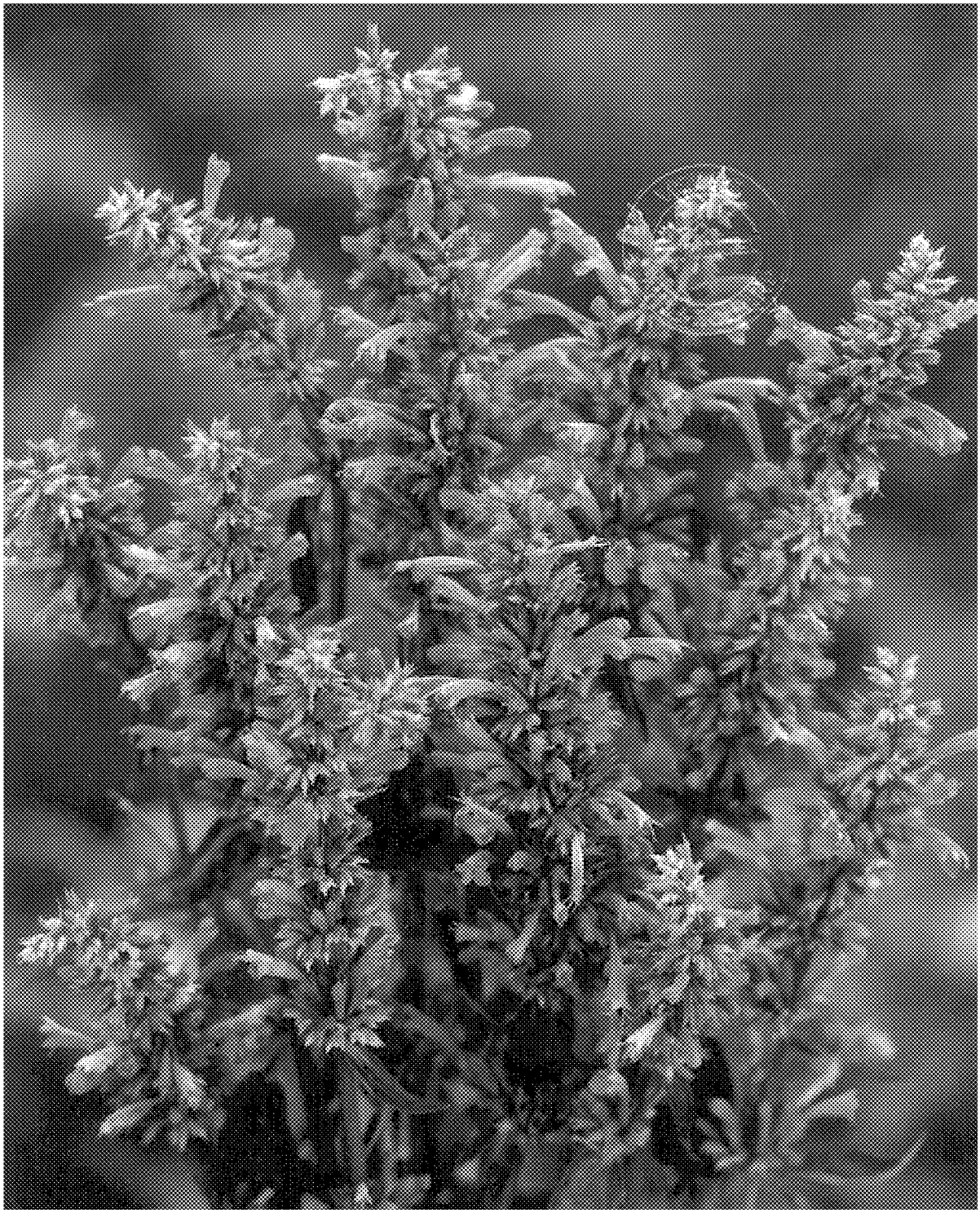

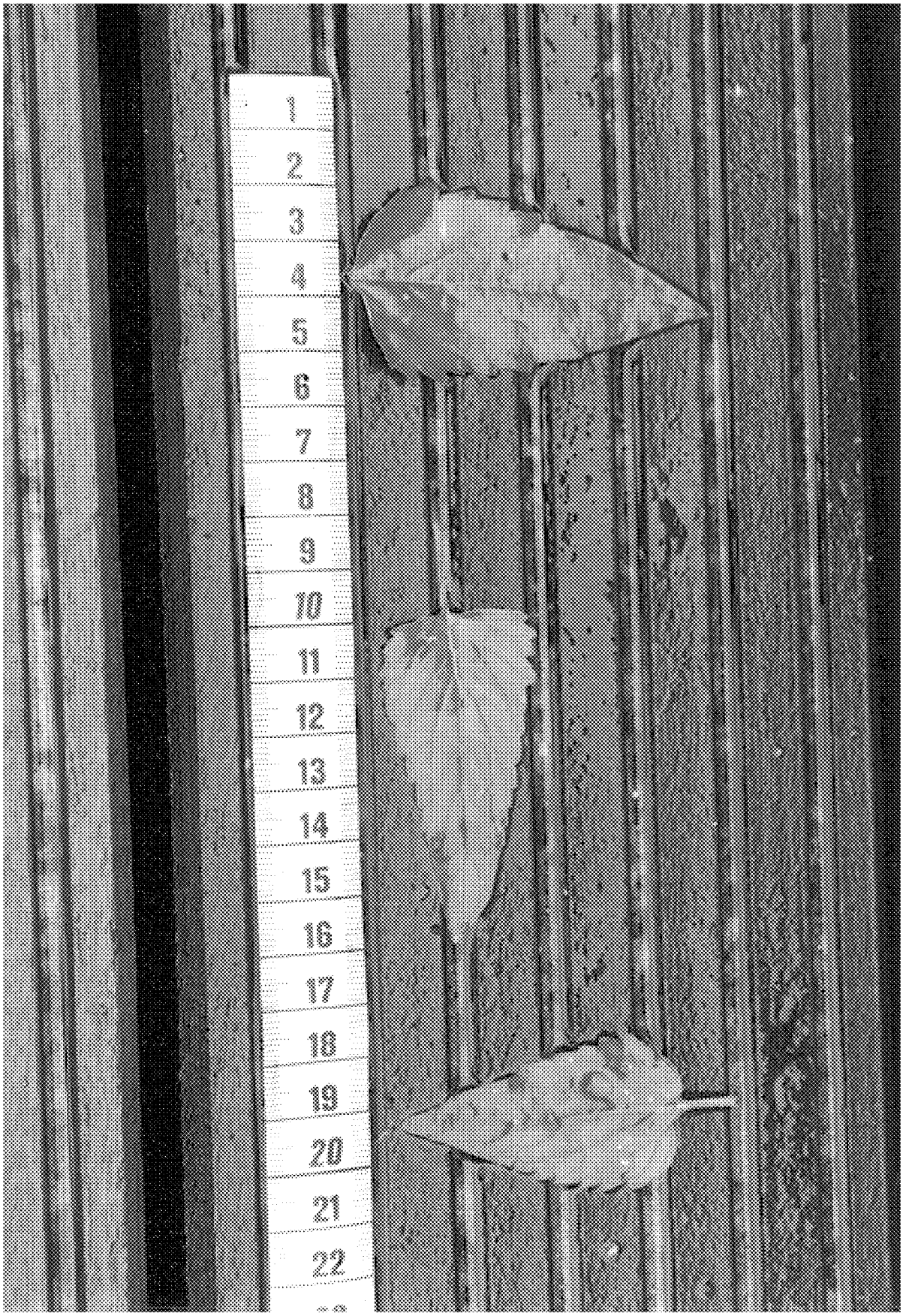
1
2
3
4
5
6
7
8
9
10
11
12
13
14
15
16
17
18
19
20
21
22